United States Patent [19]
Sporn et al.

[11] Patent Number: 5,821,254
[45] Date of Patent: Oct. 13, 1998

[54] USES OF 9-CIS-RETINOIC ACIDS AND DERIVATIVES THEREOF ALONE OR IN COMBINATION WITH ANTINEOPLASTIC AGENTS IN THE PREVENTION OR TREATMENT OF CANCER

[75] Inventors: Michael B. Sporn, Bethesda; Mario A. Anzano, Silver Springs, both of Md.

[73] Assignee: The United States of America as represented by the Department of Health and Human Services, Washington, D.C.

[21] Appl. No.: 390,342

[22] Filed: Feb. 17, 1995

[51] Int. Cl.$^6$ .......................... A61K 31/20; A61K 31/445
[52] U.S. Cl. .......................... 514/324; 514/428; 514/448; 514/559
[58] Field of Search ...................................... 514/559, 324, 514/428, 448

[56] References Cited

U.S. PATENT DOCUMENTS

| | | | |
|---|---|---|---|
| 4,418,068 | 11/1983 | Jones | 424/267 |
| 5,428,017 | 6/1995 | Bollag et al. | 514/559 |

FOREIGN PATENT DOCUMENTS

| | | |
|---|---|---|
| 0552624A1 | 1/1993 | European Pat. Off. . |

OTHER PUBLICATIONS

Robeson, et al. (1955), "Chemistry of Vitamin A. XXIV. The Synthesis of Geometric Isomers of Vitamin A via Methyl β–Methylglutaconate", *J. Am. Chem. Soc.* 77:4111–4119.
Anzano, et al. (1994), "Prevention of Breast Cancer in the Rat with 9–cis–Retinoic Acid as a Single Agent and in Combination with Tamoxifen", *Cancer Research* 54:4614–4617.
Ratko, et al. (1989), "Chemopreventive Efficacy of Combined Retinoid and Tamoxifen Treatment following Surgical Excision of a Primary Mammary Cancer in Female Rats", *Cancer Research* 49:4472–4476.
Moon, et al. (1987), "Retinoids as Chemopreventive Agents for Breast Cancer", *Cancer Detection And Prevention* vol. 16, Issue 1:73–79.
Gottardis, et al. (1987), "Antitumor Actions of Keoxifene and Tamoxifen in the N–Nitrosomethylurea–induced Rat Mammary Carcinoma Model", *Cancer Research* 47:4020–4024.
Castaigne, et al. (1992), "Lower All Trans Retinoic Acid Are Effective in Acute Promylecytic Leukemia" *Blood* vol. 80, No. 10, Supp. 1, Abstract 1429.
Warrel, et al. (1992) "All–trans Retinoic Acid (RA) For Remission Induction of Acute Promylecytic Leukemia (APL) Results Of The New York Study" *Blood* vol. 80, No. 1 Suppl. Abstract #1430.

Legha, M.D., et al. (1978), "Hormonal Therapy of Breast Cancer: New Approaches and Concepts", *Annals of Internal Medicine* 88:69–77.
Smith, et al. (1992), "Retinoids in Cancer Therapy" *Journal of Clinical Oncology*, vol. 10, No. 5:839–864.
Moon, et al. (1994), "Retinoids and Cancer in Experimental Animals" *The Retinoids; Biology Chemistry and Medicine* 2nd Edition. Edited by Sporn Roberts and Goodman. Raven Press Ltd. NY—Chapter 14.
Hong, et al. (1994), "Retinoids and Human Cancer" *The Retinoids: Biology Chemistry and Medicine* 2nd Edition. Edited by Sporn, Roberts and Goodman. Raven Press Ltd. N.Y. Chapter 15.
Early Breast Cancer Trialists Collaborative Group (1992), "Systemic treatment of early breast cancer by hormonal, cytotoxic, or immune therapy", *The Lancet*, vol. 339, No. 8785.
Early Breast Cancer Trialists Collaborative Group (1988), "Effects of Adjuvant Tamoxifen and Of Cytotoxic Therapy On Mortality In Early Breast Cancer", *The New England Journal of Medicine*, vol. 319, No. 26; 1681.
Early Breast Cancer Trialists Collaborative Group (1992), "Systemic treatment of early breast cancer by hormonal, cytotoxic or immune therapy", *The Lancet* vol. 339 No. 8784:1.
Sporn (1993), "Chemoprevention of Cancer", *Lancet* vol. 342:1211.
Fugh–Berman, et al. (1992), "Tamoxifen: disease prevention or disease substitution?", *The Lancet* vol. 340:1143.
Powles (1992), "The case for clinical trials of tamoxifen for prevention of breast cancer" , *The Lancet* vol. 340:1145.
Anzano, et al. (1994), "1α, 25–Dihydroxy–16–ene–23–yne–26,27–hexafluorocholecalciferol (Ro24–5531), a New Deltanoid (Vitamin D Analogue) for Prevention of Breast Cancer in the Rat", *Cancer Research* vol. 54, No. 7:1653.
Sommers, et al. (1991), "Cell Adhesion Molecule Uvomorulin Expression in Human Breast Cancer Cell Lines: Relationship to Morphology and Invasive Capacities", *Cell Growth & Differentiation* vol. 2, No. 8:365.
Chemical Abstracts 116:143424, "Retinamides", Kochar et al, 1992.

*Primary Examiner*—Frederick Krass
*Attorney, Agent, or Firm*—Morgan & Finnegan LLP

[57] ABSTRACT

This invention relates to methods and compositions for preventing or treating cancer. Specifically this invention relates to the use of 9-cis-retinoic acid or derivatives thereof in preventing or treating cancers, in particular breast cancer. The invention also relates to compositions of 9-cis-retinoic acid or derivatives thereof and at least one other antineoplastic agent and to the use of such compositions in the prevention or treatment of cancer, in particular breast cancer.

22 Claims, 11 Drawing Sheets

FIG. 4D

USES OF 9-CIS-RETINOIC ACIDS AND DERIVATIVES THEREOF ALONE OR IN COMBINATION WITH ANTINEOPLASTIC AGENTS IN THE PREVENTION OR TREATMENT OF CANCER

FIELD OF THE INVENTION

This invention is in the field of prevention and treatment of cancer. More specifically, this invention relates to the use of 9-cis-retinoic acids and derivatives thereof for treating cancers, in particular breast cancer. This invention also relates to the use of combinations of 9-cis-retinoic acids or derivatives thereof and a antineoplastic agent for preventing or treating cancers and compositions comprising the same.

BACKGROUND OF THE INVENTION

Breast cancer is one of the most common disease affecting women accounting for the highest percentage of malignancies in women. Current estimates indicate that one in eight women who reach the age of 95 will develop breast cancer (American Cancer Society, Atlanta Ga., 1994, p. 13). Classic modalities of treating breast cancer, as for other cancers, include surgery, radiation, chemotherapy, antineoplastic agents, hormonal therapy or combination therapies. However, extended therapy with some of these agents may cause greater morbidity than the underlying disease. The current controversy over the safety and efficacy of the use of tamoxifen to prevent breast cancer in women at high risk emphasizes the need to develop new agents for suppression of carcinogenesis (Fugh-Berman, A. et al. (1992) *LANCET* 340:1143–45; Powles T. J. (1992) *LANCET* 340:1145–47). Alternate therapies for preventing or treating breast cancers are greatly needed. In the past decade or so retinoids have been evaluated as candidates for chemoprevention of cancers in general. (Sporn, M. B., and Roberts, A. B. *Cancer Res.*, 43:3034–3040, 1983; Moon, R. C., et al. Retinoids and cancer in experimental animals. In: M. B. Sporn, A. B. Roberts, D. S. Goodman (eds.), *The Retinoids: Biology, Chemistry, and Medicine,* 2nd edition, pp. 573–595, New York: Raven Press, 1994; Hong, W. K., and Itri, L. M. Retinoids and human cancer. In: M. B. Sporn, A. B. Roberts, D. S. Goodman (eds.), *The Retinoids: Biology, Chemistry, and Medicine,* 2nd edition, pp. 597–630, New York: Raven Press, 1994).

Retinoids are a large family of molecules encompassing over three thousand members. All-trans retinoic acid, a member of the retinoid family, is a morphogen that defines certain cell fates during development and has the potential to treat cancer by inducing tumor cell differentiation (Petkovich, M. (1992) *Ann. Rev. Nutr.* 12:443–471; Thaller, C., et al. (1991) In *Retinoids: 10 Years On* 89–108 J. H. Saurat (ed) Karger/Basel). Retinoic acid binds the retinoic acid receptor (RAR) causing it to form heterodimers with the retinoid X receptor (RXR) and induce gene transcription (Chambon, P., et al. (1991) "The family of retinoid acid nuclear receptors" In *Retinoids: 10 Years On.* 10–27 J. H. Saurat (ed), Karger/Basel; Kliewer, S. A., et al. (1992) *Nature.* 355:446–449; Zhang, X. K., et al. (1992) *Nature.* 355:441–446). In addition to the well accepted role of retinoids in transcription activation, some retinoids may have direct effects on cell second messengers (Evain-Brion, D., et al. (1991) "Retinoid Acid & Cellular Signal Transduction" In *Retinoids: 10 Years On.* 46–55; J. H. Saurat(ed) Karger/Basel). Retinoid toxicity however is a major concern in long term chemoprevention studies. For example, chronic dietary administration of high doses of retinoic acid results in the accumulation of retinyl esters in the liver a process often accompanied by hepatic toxicity (Moon et al. (1992) *Cancer Detection and Prevention* 16:(1)73–79). Additional chemoprevention therapies that allow lower dosages of antineoplastic drugs, thereby mitigating potential side effects of such antineoplastic agents are greatly needed. In addition, combination chemoprevention is emerging as an important therapy in the clinical setting (Sporn, M. B. (1980) *Nature* (London) 287:107–108; Sporn, M. B. (1993) *The Lancet* 342:1211–1213), agents which enhance the activity of existing antineoplastic agents would greatly facilitate cancer treatment.

SUMMARY OF THE INVENTION

This invention relates in general to methods and compositions for preventing or inhibiting the growth of malignant cells of various types. More specifically, this invention provides a method of treating or preventing cancers, in particular breast cancer, using 9-cis-retinoic acid or 9-cis-retinoic acid derivatives or combinations of 9-cis-retinoic acids or derivatives thereof and at least one other antineoplastic agent. This invention also provides pharmaceutical compositions comprising the same.

It is an object of this invention to provide a method for preventing or treating cancers, in particular breast cancer.

It is another object of this invention to provide a method of preventing or treating cancers by administering a therapeutically effective dose of 9-cis-retinoic acid or derivatives thereof.

It is a further object of this invention to provide a method of preventing or treating cancers by administering a therapeutically effective amount of a 9-cis-retinoic acid and at least one other antineoplastic agent.

It is yet another object of this invention to provide a method for treating breast cancer by administering a therapeutically effective amount of a 9-cis-retinoic acid or derivatives thereof and at least one other antineoplastic agent.

It is yet another object of this invention to provide pharmaceutical compositions for use in the methods described herein.

It is a further object of this invention to provide a kit or drug delivery system comprising the compositions for use in the methods described herein.

DESCRIPTION OF THE FIGURES

FIG. 1A. NMU was injected into 48 rats, which were randomized into three groups which were fed either chow diet control (■, 24 rats); or 9-cis-retinoic acid (9-cis-RA), 120 mg/kg diet (●, 12 rats); or 9-cis-RA, 60 mg/kg diet (Δ, 12 rats), beginning one week after NMU. Feeding of 9-cis-RA was continued for the remainder of the experiment in the latter two groups. Tumors were palpated twice weekly and confirmed at autopsy.

FIG. 1B. As in FIG. 1A, rats were fed either chow diet control (■, 24 rats); or Tamoxifen (TAM), 0.5 mg/kg diet (◊, 12 rats); or 9-cis-RA, 60 mg/kg diet plus TAM, 0.5 mg/kg diet (▲, 12 rats). Latency curve for 9-cis-RA alone is shown in FIG. 1A.

FIG. 1C. As in 1A, rats were fed either chow diet control (■, 24 rats); or all-trans-retinoic acid (atRA), 120 mg/kg diet (●, 12 rats); or atRA, 60 mg/kg diet (Δ, 12 rats).

FIG. 3A. Effects of 9-cis-RA and Raloxifene on Breast Tumor Incidence. Rats were fed either chow diet control (■, 24 rats); or Raloxifene Hi (60 mg/kg of diet) diet (●, 12 rats); or 9-cis-RA (Δ, 12 rats); or Raloxifene Hi and 9-cis-RA (▲, 12 rats).

FIG. 3B. Effects of 9-cis-RA and Raloxifene on Breast Tumor Load. Rats were fed either chow diet control (■, 24 rats); or Raloxifene Hi (60 mg/kg of diet) (●, 12 rats); or 9-cis-RA (Δ, 12 rats); or Raloxifene-Hi and 9-cis-RA (▲, 12 rats).

FIG. 3C. Effects of Raloxifene and 9-cis-Retinoic Acid on Breast Tumor Incidence. Rats were fed either chow diet control (■, 24 rats); or Raloxifene-Lo diets (○, 12 rats); or 9-cis-RA (Δ, 12 rats); or Raloxifene-Lo diet and 9-cis-RA (●, 12 rats).

FIG. 3D. Effects of 9-cis-RA and Raloxifene on Breast Tumor Load. Rats were fed either chow diet control (■, 24 rats); Raloxifene-Lo diets (○, 12 rats); 9-cis-RA (Δ, 12 rats); or Raloxifene-Hi diets and 9-cis-RA (●, 12 rats).

FIG. 4A. Shows the percent of tumor incidence over days of treatment. Rats were fed either chow diet control (■, 24 rats); or 9-CE-HI (●, 12 rats); or TAM (Δ, 12 rats); or TAM+9CE-HI (▲, 12 rats).

FIG. 4B. Shows the numbers of tumors in rats over days of treatment. Rats were fed chow control diet (■, 24 rats); or 9-CE-Hi (●, 12 rats); or TAM (Δ, 12 rats); or TAM and 9CE-Hi (▲, 12 rats).

FIG. 4C. Shows the percent of tumor incidence over days of treatment. Rats were fed chow control diet (■, 24 rats); or 9CE-Lo (○, 12 rats); or TAM (▲, 12 rats); or TAM+9CE-Lo (●, 12 rats).

FIG. 4D. Shows the number percent of tumors in rats over days of treatment. Rats were fed chow control diet (■, 24 rats); or 9CE-Lo (○, 12 rats); or TAM (▲, 12 rats); TAM+9CE-Lo (●, 12 rats).

DETAILED DESCRIPTION OF THE INVENTION

The present invention provides a method of inhibiting or preventing the growth of malignant cells by exposing cells to 9-cis-retinoic acid (9-cis-RA) or derivatives thereof or 9-cis-retinoic acid or derivative thereof and at least one other antineoplastic agent. This method is based on an observation by the inventors that 9-cis-retinoic acid (9-cis-RA), or derivatives thereof are highly effective in preventing breast cancer in an animal model and that 9-cis-RA is superior to all-trans-retinoic acid (atRA) for this purpose, and further that 9-cis-RA enhances the chemopreventive activity of estrogen modulating drugs.

The present invention relates to the use of 9-cis-retinoic acid or derivatives thereof in the prophylactic and therapeutic treatment of cancer caused by malignant cells of various types. 9-cis-retinoic acid as used herein has the formula:

This retinoic acid and synthesis thereof are described in C. D. Robeson et al., *J. Am. Chem. Soc* 77:4111 (1955) and Frickel, F., "Chemistry and Physical Properties of Retinoids: *The Retinoids* Sporn, Roberts, Goodman (eds) Academic Press p 7–145 (1984).

Cancer as used herein includes, but is not limited to, malignant tumors, adenocarcinomas, carcinomas, sarcomas, malignant neoplasms, and leukemias. In particular epithelial cell derived cancers are intended to be encompassed by this invention. Examples of epithelial cell derived cancers that may be treated by the methods described herein include, but are not limited to, breast cancer, colon cancer, ovarian cancer, lung cancer or prostate cancer. In a preferred embodiment, breast cancer is treated by the methods and compositions described herein. Such cancers may be caused by, chromosomal abnormalities, degenerative growth and developmental disorders, mitogenic agents, ultraviolet radiating (UV), viral infections, oncogenes, mutations in genes, in-appropriate expression of a gene and presentation on a cell, or carcinogenic agent.

Administration of the pharmaceutical composition comprising 9-cis-retinoic acid or derivatives thereof encompassed by this invention may be for either a prophylactic or therapeutic use. When provided prophylactically, 9-cis-retinoic acid or derivatives thereof is provided in advance of any symptoms due to the cancer afflicting the individual. The prophylactic administration of the composition is intended as a chemopreventive therapy and serves to either prevent initiation of malignant cells or arrest or reverse the progression of transformed premalignant cells to malignant disease. When provided therapeutically the composition is provided at or after the onset of the disease. The therapeutic administration of the composition of this invention serves to attenuate or alleviate the cancer or facilitate regression of the cancer afflicting the individual. The term individual is intended to include any animal, preferably a mammal, and most preferably a human. Veterinary uses are intended to be encompassed by this definition.

In one embodiment of this invention, individuals at high risk for a particular cancer, or at high risk of reoccurrence of a cancer or who have known risk factors are prophylactically treated with the methods and compositions described herein. By way of example, such individuals may include those with a familial history for either early or late onset of breast cancer, individuals carrying deleterious mutations in the BRCAL gene (Miki et al. (1994) *Science* 266:66–71), women at risk of occurrence of second primary breast carcinomas, women having genetic or other high risk factors or for post-disease prophylaxis. General ranges of suitable effective prophylactic dosages that may be used are about 0.1 mg/kg of body weight per day to about 1000 mg/kg/day, a preferred range is about 0.5 mg/kg/day to about 500 mg/kg/day, most preferred is about 1 mg/kg/day to about 100 mg/kg/day. The daily dose of the compound may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein.

In an alternative embodiment a derivative of 9-cis-retinoic acid may be used either prophylactically or therapeutically to treat a individual afflicted with cancer. Derivatives are intended to include any compounds which are structurally related to 9-cis-retinoic acid or which possess the substantially equivalent biological activity of 9-cis-retinoic acid. Derivatives of 9-cis-retinoic acid which are capable of enhancing the activity of antineoplastic agents, such as Tamoxifen and Raloxifene, are also intended to be encompassed by this invention. In a preferred embodiment a derivative may have the general formula:

Wherein R is COR' in which R'=OR"or NHR", wherein R"=$C_1$-$C_6$ alkyl. Of particular interest are the amidated 9-cis-retinoic acid derivatives (R=NHR"). Examples of 9-cis-retinoic acid derivatives include, but are not limited to, 9-cis-retinoic acid ethylamide (9CE) (R=CONHC$_2$H$_5$). General dosage ranges for 9-cis-retinoic acid derivatives in prophylactic and therapeutic use may be about 0.1 mg/kg/day to about 1000 mg/kg/day, or preferably about 0.5 mg/kg/day to about 500 mg/kg/day, or most preferred, about 1 mg/kg/day to about 100 mg/kg/day. Dosages may need to be optimized for the individual patient. The 9-cis-retinoic acid derivatives of this invention can be synthesized by conventional methods known to one skilled in the art. Combinations of 9-cis-retinoic acid and one or more derivatives may also be used in the prophylactic and therapeutic applications. By way of example 9-cis-retinoic acid and 9-cis-retinoic acid ethylamide may comprise a pharmaceutical composition for use in the methods described herein.

This invention also provides a method of enhancing the activity of antineoplastic agents against malignant cells comprising administering to individuals in need of treatment, a therapeutically effective amount of 9-cis-retinoic acid or derivative thereof and another antineoplastic agent. The use of 9-cis-retinoic acid or derivatives thereof in combination with at least one other antineoplastic agent may be used in the prophylactic or therapeutic treatment of cancer. Examples of antineoplastic agents include, but are not limited to, drugs, chemicals, or hormones which prevent the initiation of malignant cells or inhibit or reverse the proliferation of malignant cells or prevent transformation of cells. In a particular embodiment hormonally sensitive cancers may be treated by the methods and compositions disclosed herein. Such cancers may include, but are not limited to, some breast cancers or prostate cancers. By way of example, the estrogen receptor status of primary and metastatic breast cancer has been demonstrated to be of therapeutic and prognostic significance ("Essentials of Obstetrics and Gynecology"(1986) W. B. Saunders Company, Philadelphia, Pa.; Chapter 39). Examples of hormonal modifying agents that have been used to prophylactically or therapeutically to treat breast cancers include, but are not limited to, the estrogen modifying drugs such as [Z]-2[4-(1,2-Diphenyl-1-butenyl)-phenoxy]-N, N-dimethyl-ethanamine (Tamoxifen) and derivatives thereof (Merck Index, (1989) 11th Edition, S. Budavari(ed) Merck & Co. Rahway, N.J.; British Patent No. 1,013,907; U.S. Pat. No. 4,536,516); or 6-hydroxy-2-(4-hydroxyphenyl)-3[4-(2-piperidinoethoxy) benzoyl] benzo [b]thiophene (Raloxifene; Eli Lily and Company, Indianapolis, Ind.), esters, ethers and derivatives thereof as described in U.S. Pat. No. 4,418,068 which is herein incorporated by reference. When 9-cis-retinoic acid or derivatives thereof are used in combination with another antineoplastic agent, the 9-cis-retinoic acid or derivative thereof may be administered prior to, concurrently or after the administration of the antineoplastic agent.

The dosing regimes and schedules used in clinical trials for testing of the antineoplastic agent may be used as a general guideline for doses of the antineoplastic agent to be used in combination with 9-cis-retinoic acid or derivative thereof. For example, in clinical trials Tamoxifen has been used in ranges of about 20 to 40 mg/day for periods ranging from less than one year to two years, the standard dose being about a 20 mg daily dose. (Early Breast Cancer Trialists' Collaborative Group, *New England Journal of Medicine* (1988) 319:1681–1692); Early Breast Cancer Trialists' Collaborative Group (1992) *The Lancet* 339:71–85; Early Breast Cancer Trialists' Collaborative Group (1992) *The Lancet* 339:1–15) Suggested dosages for Raloxifene and derivatives thereof are provided in U.S. Pat. No. 4,418,068. The general range of effective administration rates provided for Raloxifene and derivatives thereof is from about 0.05 mg/kg/day to about 50 mg/kg/day with a most highly preferred range of about 0.1 mg to about 5 mg/kg/day. (U.S. Pat. No. 4,418,068). The dosing regimes and schedules used in clinical trials or provided in the literature may be used as a general guideline for doses of the estrogen modifying drug to be used in conjunction with 9-cis-retinoic acid or derivatives thereof. It is anticipated that a lower dosage for these estrogen modulating drugs may be effective when used in combination with 9-cis-retinoic acid or derivative thereof. Examples of effective dosages for 9-cis-retinoic acid or 9-cis-retinoic acid derivatives that may be used when combined with another neoplastic agent are about 0.1 mg/kg/day to about 1,000 mg/kg/day, preferably about 0.5 mg/kg/day to about 500 mg/kg/day. Most preferred is about 1 mg/kg/day to about 100 mg/kg/day. One of skill in the art will appreciate that the dosage of the 9-cis-retinoic acid or derivative thereof and the dosage of the estrogen modifying drug may need to be optimized for each individual. By way of example, compositions of 9-cis-retinoic acid and Tamoxifen or 9-cis-retinoic acid and Raloxifene may be used in the methods described herein. In yet another embodiment, a combination of 9-cis-retinoic acid, Tamoxifen and Raloxifene may be used in the methods described herein.

In yet another embodiment 9-cis-retinoic acid or its derivative may be administered to a mammal preferably a human, afflicted with breast cancer. The composition may be administered at a dose of about 0.1 mg/kg day to about 1000 mg/kg daily, most preferably about 0.5 mg/kg to about 500 mg/kg, most preferred about 1 mg/kg/day to about 100 mg/kg/day. However, the method of treatment is in no way limited to a particular concentration or range of 9-cis-retinoic acid or derivative thereof and may be varied for each individual being treated and for each derivative used. The composition is administered at intervals or continuously until a clinical change in the disease can be detected. Such clinical parameters that may be assessed include, but are not limited to, tumor size, alteration in the level of tumor markers used in clinical testing for particular malignancies. Based on such parameters the treating physician will determine the therapeutically effective amount of 9-cis-retinoic acid or derivative thereof to be used for a given individual. Such therapies may be administered as often as necessary and for the period of time judged necessary by the treating physician.

In yet another alternative embodiment 9-cis-retinoic acid or a derivative thereof and at least one other antineoplastic agent may be administered to an individual afflicted with cancer. In a preferred embodiment, breast cancer is treated with 9-cis-retinoic acid or derivatives thereof and a antineoplastic agent. Preferred combinations are 9-cis-retinoic acid and Tamoxifen or 9-cis-retinoic acid and Raloxifene. By way of example, 9-cis-retinoic, in combination with Tamoxifen and Raloxifene may also be used. Effective dosages may be similar as those described for prophylactic use.

The compositions directed against mammalian cancers may be evaluated first in animal models, initially rodents and finally in humans. The safety of the compositions and methods of treatment is determined by looking for the effect of treatment on the general health of the treated animal (weight change, fever, appetite behavior etc.) monitoring of generalized toxicity, electrolyte renal and hepatic function, hematological parameters and function measurements. Pathological changes may be detected on autopsies. After initial testing in animals, cancer patients can be tested. Conventional methods are used to evaluate the response of the patient to determine the efficacy of the compositions.

The retinoic acid or derivative thereof or the 9-cis-retinoic acid and derivative thereof and the antineoplastic agent may be supplied in kit form for use in the methods described herein. The kit may contain each component separately or each component combined to form a composition. Other components may be added to the kit, for example, additional chemotherapeutic drugs or immunosuppressive drugs and the like. The kit or drug delivery system may also contain instructions regarding administration and suggested ranges to be used in administering the composition.

While it is possible for the composition comprising 9-cis-retinoic acid or derivatives thereof or combinations of 9-cis-retinoic acid or derivatives thereof and at least one other antineoplastic agent to be administered in a pure or substantially pure form or to administer each component in pure or substantially pure form, it is preferable to present it as a pharmaceutical composition, formulation or preparation.

The formulations of the present invention, both for veterinary and for human use, comprise each component individually or as a composition as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharide, amino acids, inorganic acids, and organic acids which may be used either on their own or as admixtures. These stabilizers are preferably incorporated in an amount of 0.11–10,000 parts by weight per part by weight of each component or the composition. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating each component separately or as a composition of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the 9-cis-retinoic acid or derivatives thereof alone or in combination with antineoplastic agents thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy. As adjunct therapy 9-cis-retinoic acid or derivatives thereof may be administered alone or in conjunction with an antineoplastic agent. In a preferred embodiment 9-cis-retinoic acid in combination with either the estrogen modifying drug Tamoxifen or derivatives thereof and/or Raloxifene or derivatives thereof is used as adjunct therapy. Preferably Tamoxifen or Raloxifene are used.

All books, articles, or patents referenced herein are incorporated by reference. The following examples illustrate to various aspects of the invention but are in no way intended to limit the scope thereof.

EXAMPLE 1

Prevention of Breast Cancer in the Rat with 9-Retinoic Acid as A Single Agent and In Combination with Tamoxifen

Materials and Methods

Mammary Carcinogenesis Studies

A standard protocol for induction of breast cancer in Sprague-Dawley rats was used (Moon, R. C., et al., *Cancer Res.*, 39:1339–1346, (1979); Anzano, M. A., et al., *Cancer Res.*, 54:1653–1656, (1994)), with a single i.v. dose of N-nitroso-N-methyl-urea (NMU), 50 mg/kg body weight. All palpated tumors were confirmed at autopsy. Retinoids and tamoxifen (TAM) were incorporated into powdered lab chow as described previously (Anzano, M. A., et al., *Cancer Res.*, 54:1653–1656, 1994), and fed *ad libitum,* beginning one week after injection with NMU. 9-cis-retinoic acid (9-cis-RA) (Kuraray Chemical, Osaka, Japan) or all-trans retinoic acid (atRA) (Hoffmann-La Roche, Nutley, N.J.) were fed at either of 2 doses, 120 mg (high dose) or 60 mg (low dose)/kg of diet; TAM (Sigma Chemical, St. Louis, MO) was fed at either 1.0 mg (high dose) or 0.5 mg (low dose)/kg of diet. Conventional methods for statistical analysis were used as described in Anzano, M. A., et al., *Cancer Res.*, 54:1653–1656, (1994).

Cell Culture Studies and *Immunohistochemistry of E-cadherin*

Human breast cancer cells were cultured as described (Anzano, M. A., et al., *Cancer Res.*, 54:1653–1656, 1994). To measure induction of E-cadherin (E-cad), SK-BR-3 (American Type Tissue Culture Collection; ATCC) cells were treated with either 9-cis-RA or atRA ($10^{-7}$M) for 48 hours (h) prior to fixation in cold methanol. Immunocytochemical staining of E-Cadherin (E-cad) was performed by conventional methodology as described in Sommers, C. L., et al., *Cell Growth Differ.*, 2:365–372, (1991), using an antibody (anti-GP-84) [Sommers, C. L., et al., *Cell Growth Differ.*, 2:365–372, (1991)] directed against the extracellular domain of E-cad.

Inhibition of mammary carcinogenesis

Greater than 90% of Sprague-Dawley rats treated with NMU alone (50 mg/kg body weight) develop invasive mammary adenocarcinomas within 3 to 4 months of a single i.v. injection. Results were obtained on a total of 252 rats treated with NMU, using either 9-cis-RA or atRA alone, or in combination with TAM, to inhibit the development of mammary carcinoma. TAM was chosen because of the current ongoing clinical trials being conducted in thousands of women world-wide, evaluating the efficacy of this agent for prevention of breast cancer. At optimal doses, TAM is highly effective in the NMU rat model (Gottardis, M. M., and Jordan, V. C. *Cancer Res.*, 47:4020–4024, 1987). To evaluate additive or synergistic effects of the combination of either 9-cis-RA or atRA with TAM, suboptimal doses of TAM were used.

Figure 1A:
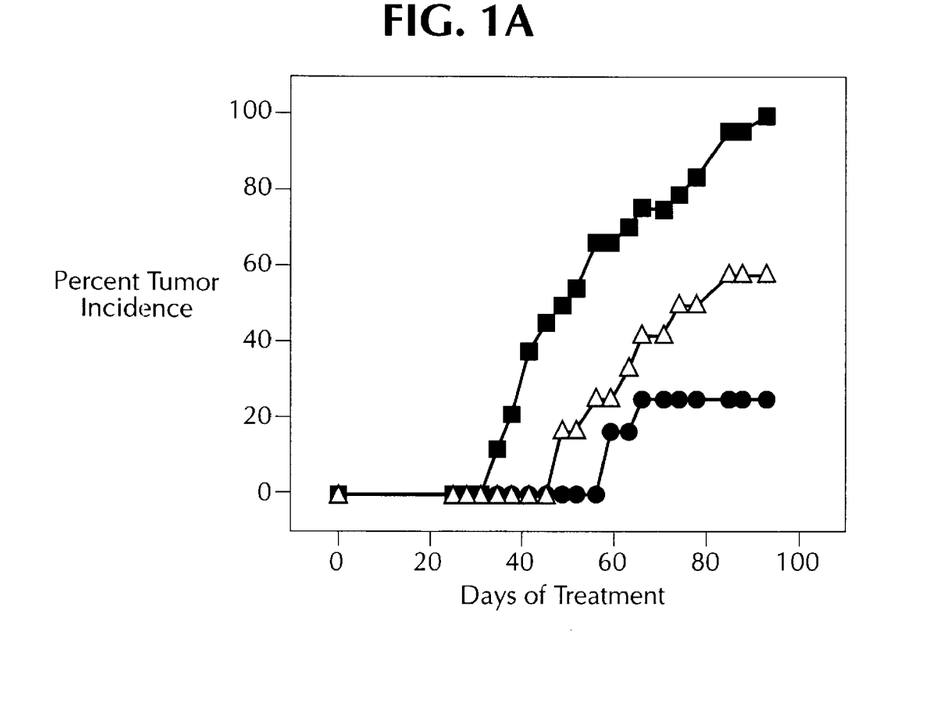
FIGS. 1A–1C show percent of tumor incidence in rats over days of treatment.
Figure 1B:
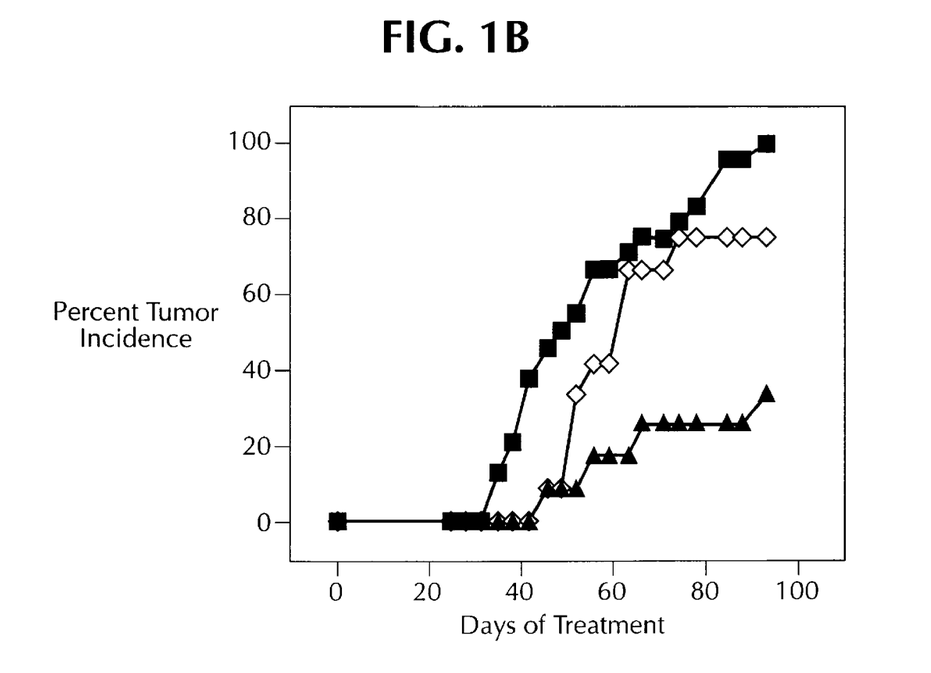
Figure 1C:
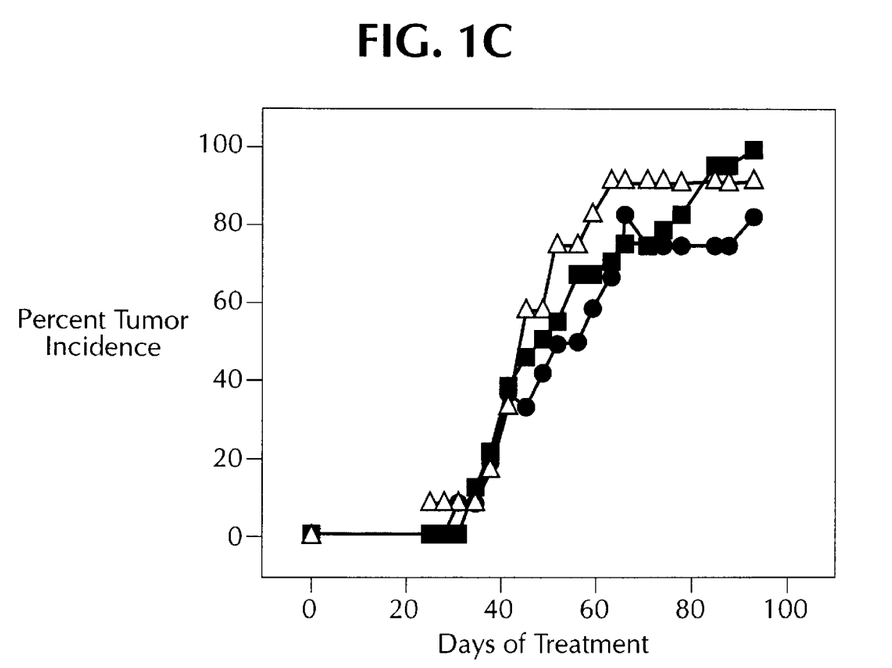

Two separate experiments were performed, and the results are shown in Table 1 and FIGS. 1A–1C. In all cases, treatment with chemopreventive agents began 1 week after a single i.v. injection of NMU. The data indicate that 9-cis-RA is highly effective and in particular, that it is markedly superior to atRA, both as a single agent and in combination with TAM. Chronic feeding of 9-cis-RA caused significant suppression of carcinogenesis, as measured by four end-points, namely tumor incidence, average number of tumors per rat, and average tumor burden (the total weight of all of an animal's tumors), and tumor latency. The effect of 9-cis-RA on the number of rats that were tumor-free at autopsy is particularly striking: in the two experiments (Table 1), only 1 of 48 (2%) of the control rats treated with NMU alone was tumor-free, while 24 of 48 (50%, P<0.001) of the rats treated with NMU plus 9-cis-RA had no grossly detectable tumors. In addition, statistical analysis indicates that the effects of 9-cis-RA on inhibition of tumor number and tumor burden are also highly significant (P<0.001 at the higher dose of 9-cis-RA, and 0.002 or less at the lower dose of 9-cis-RA). FIG. 1A also shows that 9-cis-RA greatly increases tumor latency. In contrast, only 3 of 24 (13%) of the rats treated with atRA (Experiment 1, Table 1) were tumor-free at autopsy, and atRA had no significant effect on tumor number and tumor burden, or on tumor latency (FIG. 1C).

In addition to studying its efficacy as a single agent, it was determined whether 9-cis-RA would provide additional benefit when combined with TAM. Tables 1 and 2, as well as FIG. 1B, show that 9-cis-RA adds statistically significant benefit to a TAM regimen, using the same three end-points that were evaluated for single agents. Pooling the results of experiments 1 and 2 (as shown in Table 2) indicates that the higher dose of 9-cis-RA, when added to TAM, doubles the number of rats that are tumor-free at autopsy (P=0.009 for the comparison of the combination of 9-cis-RA plus TAM against TAM alone), decreases average number of tumors/ rat from 1.3 to 0.2 (P<0.001), and decreases average tumor burden from 3.5 g to 0.3 g (P=0.001), or the 75th percentile of the tumor burden distribution from 5.0 g to 0.1 g (P=0.001). Smaller but highly significant effects are also seen for the addition of the lower dose of 9-cis-RA to the low dose of TAM. Finally, when all 72 animals treated with the combination with 9-cis-RA (at either dose) plus TAM (at either dose) are compared with all 36 animals treated only with TAM alone (at either dose), the P values for the efficacy of adding 9-cis-RA to TAM are all 0.001 or less, whether one measures effects on inhibition of tumor incidence, inhibition of average number of tumors/rat, or on average tumor burden. None of the chemopreventive agents caused any grossly evident toxicity. Although there was some slightly diminished weight gain in animals fed 9-cis-RA, atRA, or TAM, the average weights of rats on chemopreventive regimens were always 85% or greater of those fed chow diets alone. Furthermore, since rats fed atRA had equivalent growth curves, the beneficial effects of 9-cis-RA cannot be ascribed to effects on total caloric intake.

reported previously, (Lacroix, A., and Lippman, M. E. *J. Clin. Invest.* 65:586–591, 1980; Fontana, J. A., et al. J. Natl. Cancer Inst. 78:1107–1112, 1987; reviewed in Gudas, L. J., Sporn, M. B., and Roberts, A. B. Cellular biology and biochemistry of the retinoids. In: M. B. Sporn, A. B. Roberts, D. S. Goodman (eds.), *The Retinoids: Biology,*

TABLE 1

Prevention of mammary cancer by 9cisRA, atRA, TAM, and combinations thereof

| Treatment | Tumor-free ($P_1;P_2$) | Avg. no. tumors ($P_1;P_2$) | ATB[a] ($P_1;P_2$) |
|---|---|---|---|
| Experiment 1 | | | |
| Control | 0/24 | 3.6 | 10.9 |
| 9-cis-RA, Hi | 9/12 (<0.001) | 0.3 (<0.001) | 0.8 (<0.001) |
| 9-cis-RA, Lo | 5/12 (0.002) | 1.6 (0.002) | 4.1 (0.002) |
| atRA, Hi | 2/12 | 2.8 | 11.2 |
| atRA, Lo | 1/12 | 3.3 | 12.0 |
| TAM, Lo | 3/12 (0.03) | 1.8 (0.002) | 3.4 (0.004) |
| 9-cis-RA, Hi + TAM, Lo | 8/12 (<0.001; 0.05) | 0.3 (<0.001; 0.003) | 0.5 (<0.001; 0.01) |
| 9-cis-RA, Lo + TAM, Lo | 8/12 (<0.001; 0.05) | 0.8 (<0.001; <0.04) | 2.1 (<0.001; <0.05) |
| atRA, Hi + TAM, Lo | 5/12 (0.002; 0.33) | 0.9 (<0.001; 0.05) | 2.0 (<0.001; 0.20) |
| atRA, Lo + TAM, Lo | 6/12 (<0.001; 0.20) | 1.2 (<0.001; 0.17) | 1.3 (<0.001; 0.06) |
| Experiment 2 | | | |
| Control | 1/24 | 2.6 | 8.5 |
| 9-cis-RA, Hi | 7/12 (<0.001) | 0.6 (<0.001) | 3.2 (<0.001) |
| 9-cis-RA, Lo | 3/12 | 2.2 | 4.8 |
| TAM, Hi | 7/12 (<0.001) | 0.4 (<0.001) | 0.5 (<0.001) |
| TAM, Lo | 6/12 (0.003) | 0.8 (0.001) | 3.7 (0.01) |
| 9-cis-RA, Hi + TAM, Hi | 11/12 (<0.001; 0.08) | 0.1 (<0.001; 0.03) | 0.07 (<0.001; 0.03) |
| 9-cis-RA, Hi + TAM, Lo | 10/12 (<0.001; 0.10) | 0.2 (<0.001; 0.02) | 0.04 (<0.001; 0.03) |
| 9-cis-RA, Lo + TAM, Hi | 10/12 (<0.001; 0.18) | 0.3 (<0.001; 0.24) | 0.2 (<0.001; 0.20) |
| 9-cis-RA, Lo + TAM, Lo | 9/12 (<0.001; 0.20) | 0.3 (<0.001; 0.04) | 4.9 (0.001; 0.14) |

Figure Legend for Table 1:
[a]ATB, average tumor burden; the average weight of a rat's tumors at autopsy. In both experiments, rank sum tests were used to compare tumor burdens. $P_1$, value for the comparison of any chemopreventive treatment versus controls treated with NMU alone. $P_2$, value for the comparison of any combined retinoid + TAM treatment versus TAM alone. Doses were as follows: 9-cis-RA or atRA, Hi, 120 mg/kg diet; 9-cis-RA or atRA, Lo, 60 mg/kg diet; TAM, Hi/Lo, 1.0/0.5 mg/kg diet. In Experiment 1, agents were fed for 3 months, and in Experiment 2, agents were fed for 4.5 months. All rats were injected with NMU 1 week before starting diets.

TABLE 2

Benefit of addition of 9-cis-RA to TAM in prevention of mammary cancer

| Treatment | Tumor-free (P)[a] | Avg. No. (P) | Top quartile TB[b], g(P) |
|---|---|---|---|
| TAM, Lo | 9/24 | 1.3 | 5.0 |
| TAM, Lo + 9-cis-RA, Hi | 18/24 (0.009) | 0.2 (0.001) | 0.1 (0.001) |
| TAM, Lo + 9-cis-RA, Lo | 17/24 (0.021) | 0.5 (0.01) | 0.2 (0.023) |

Figure Legend for Table 2:
[a]P, comparison of the effects of adding 9-cis-RA to TAM, when compared to TAM alone.
[b]Top quartile tumor burden is the 75th percentile of the tumor burden distribution for animals in each particular cohort. The value for the top quartile TB in the control group which received no chemopreventive agent was 17.1 g. Rank sum tests were used to compare tumor burdens. Doses of agents as in Table 1.

Cell Culture Studies

Figure 2A:
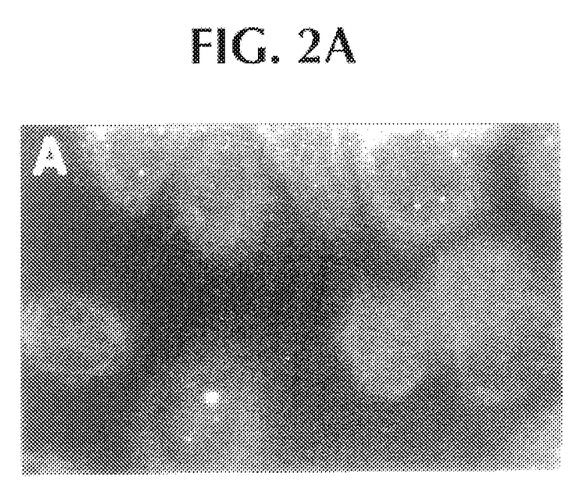
FIG. 2A–2B show immunofluorescent staining of E-cadherin (E-cad) in SK-BR-3 cells following 48 h of treatment with vehicle alone (FIG. 2A) or $10^7$ M 9-cis-RA (FIG. 2B).
Figure 2B:
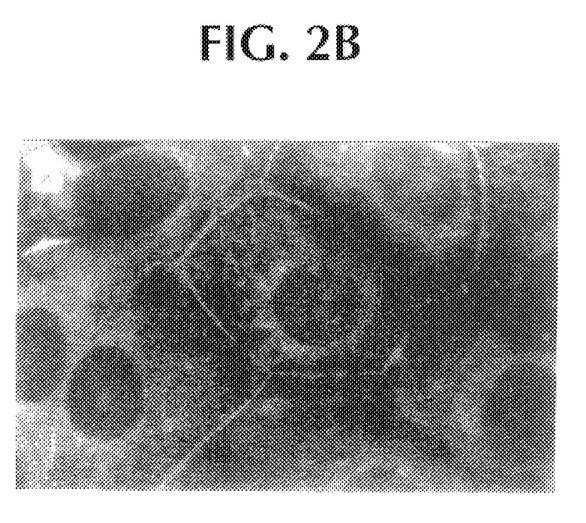
Figure 3A:
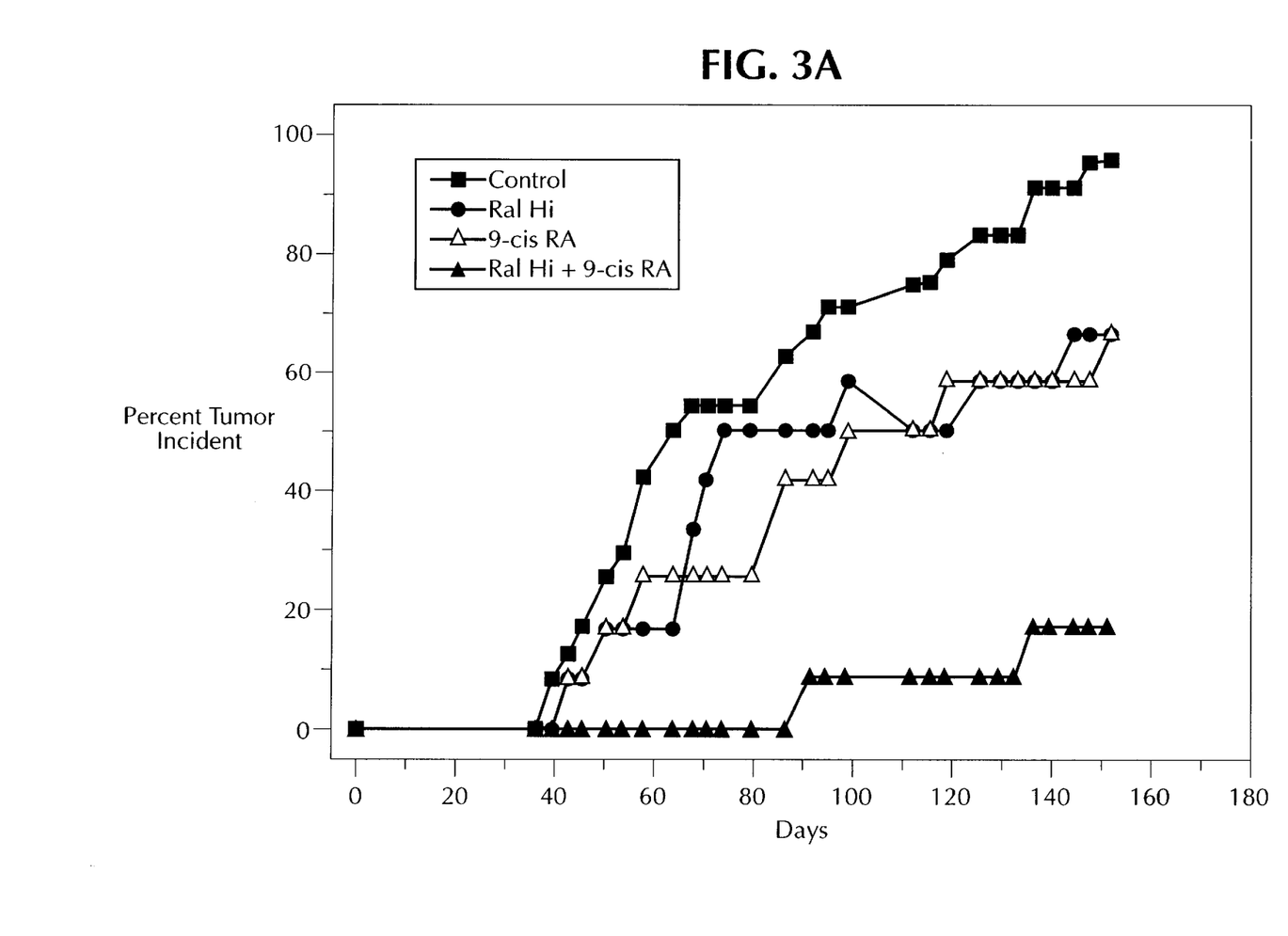
FIG. 3A–3D show the effects of Raloxifene (6-hydroxy-2-(4-hydroxyphenyl)-3-[4-(2 piperidinoethoxy) benzoyl] benzo[b] thiophene) alone or in combination with 9-cis-RA on breast tumor incidence and breast tumor load in the NMU rat breast cancer model. Rats were injected with NMU and beginning one week after NMU were fed either chow diet control, or Raloxifene-Hi (60 mg/kg of diet) alone, or Raloxifene-Lo (20 mg/kg) alone or in combination with 9-cis-RA.
Figure 3B:
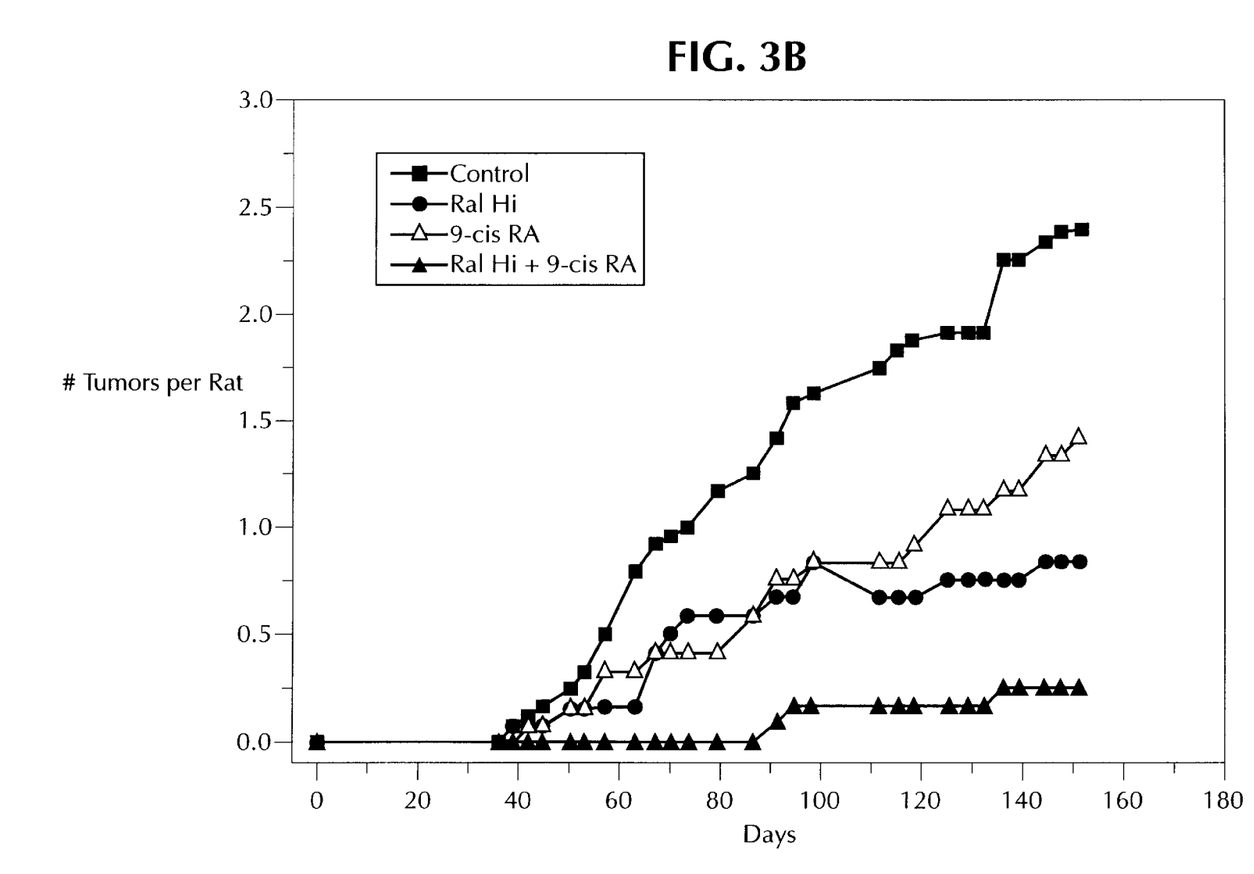
Figure 3C:
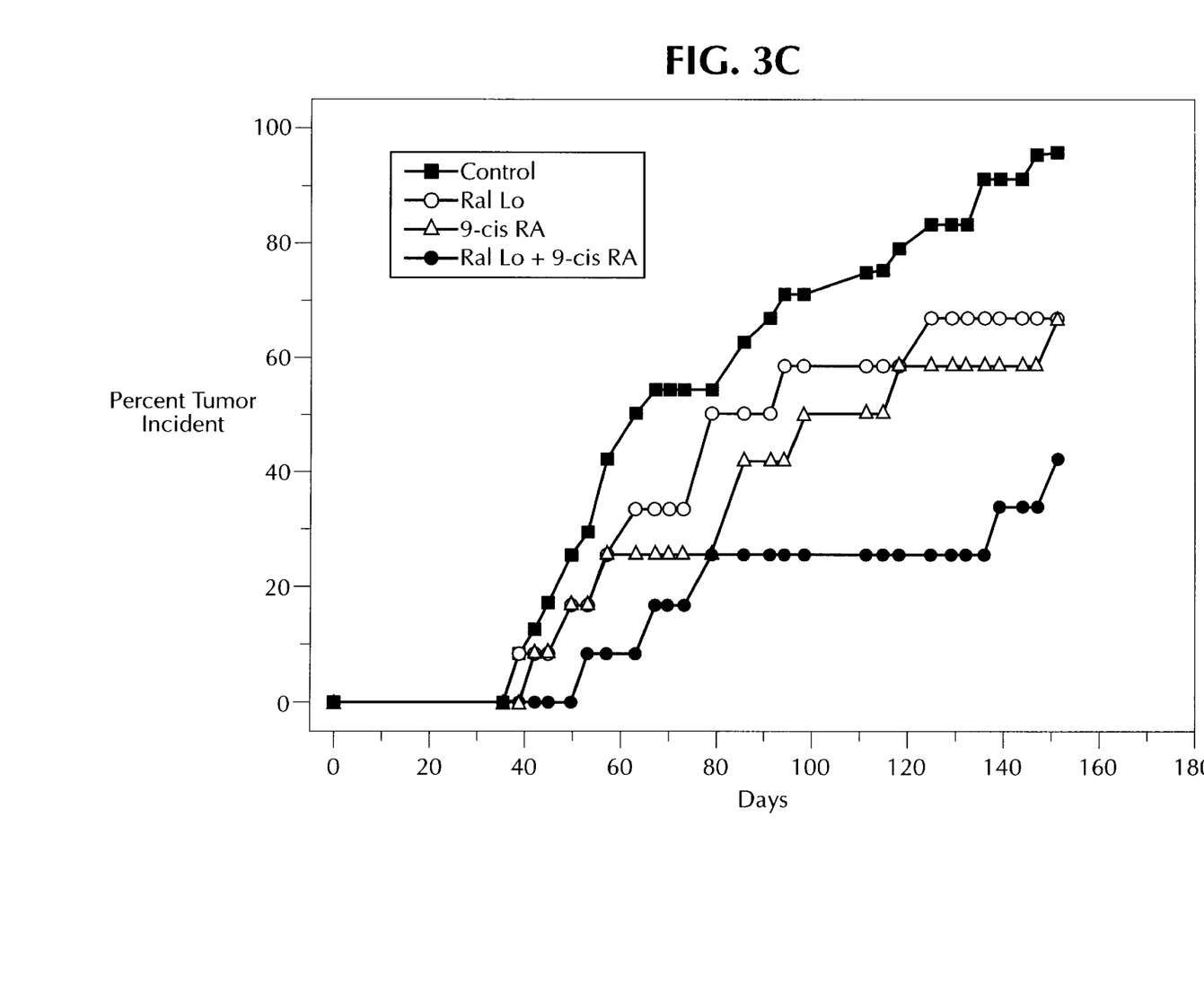
Figure 3D:
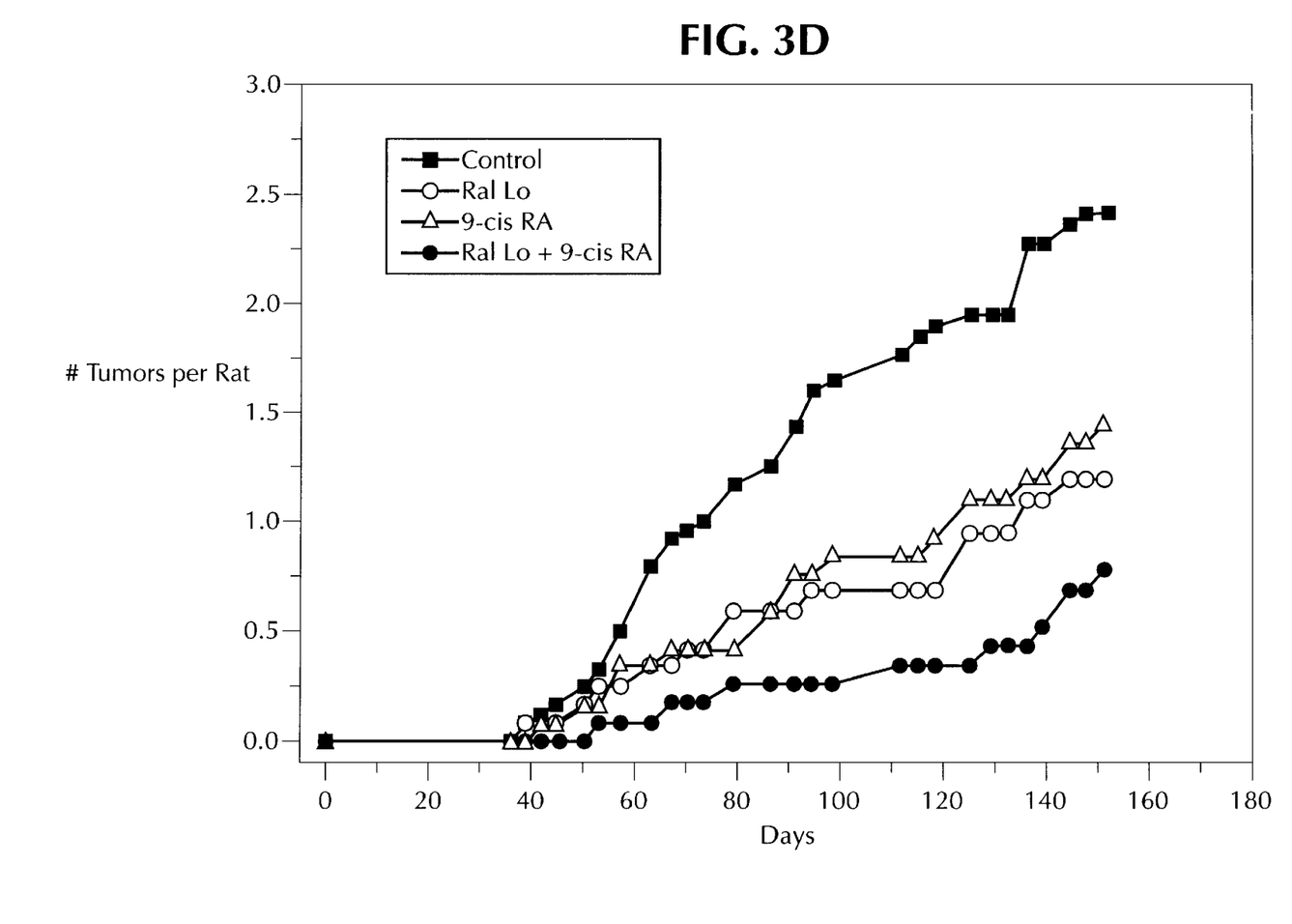
Figure 4A:
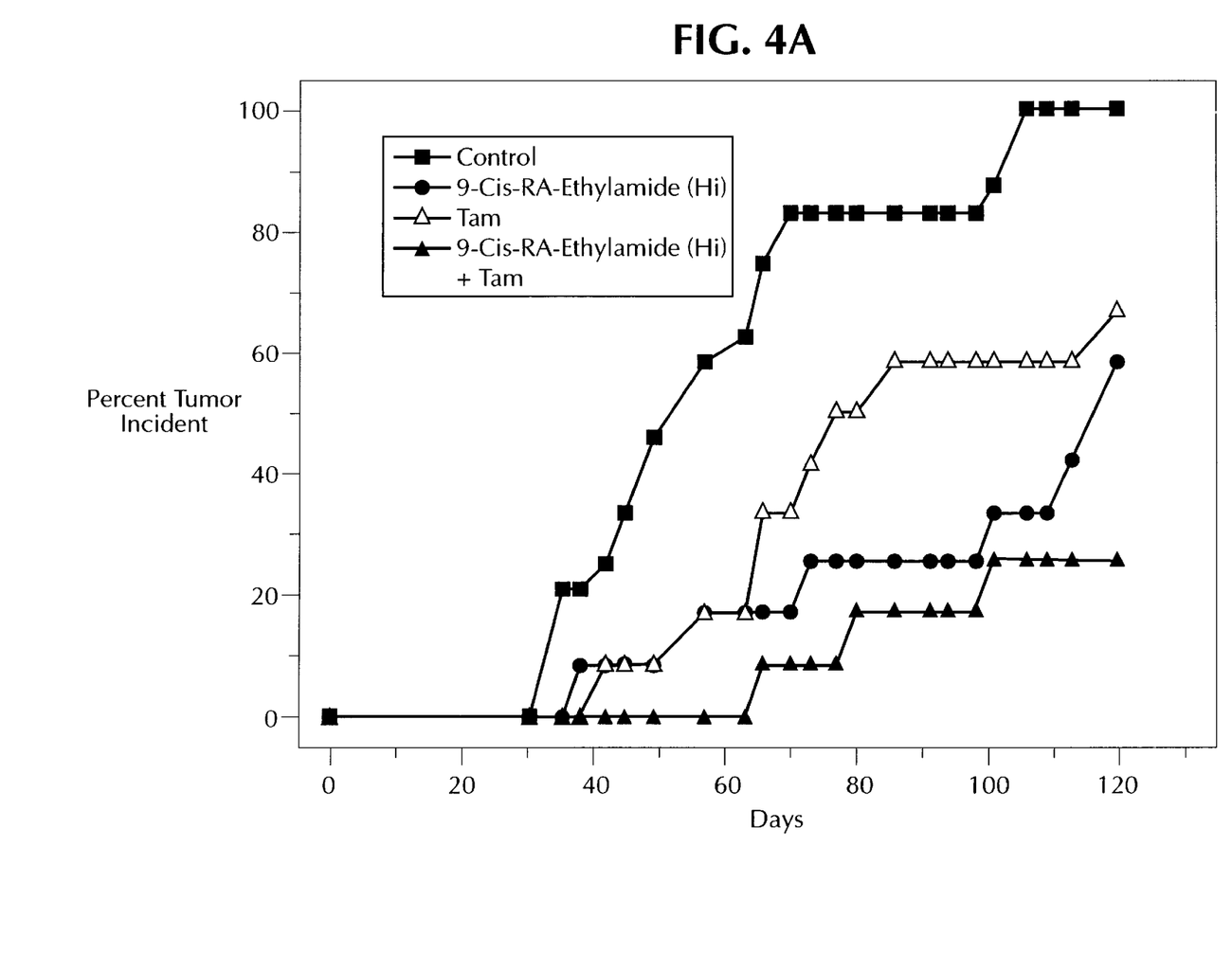
FIGS. 4A–4D show the effect of the 9-cis-retinoic acid analog, 9-cis-retinoic acid-ethylamide (9CE) in prevention of mammary carcinogenesis. Rats were injected with NMU and beginning one week after, fed either control chow diet, or a diet Hi (2 mmoles/kg of diet) or low (1 mmole/kg of diet) in 9CE alone or in combination with Tamoxifen (0.5 mg/kg diet).
Figure 4B:
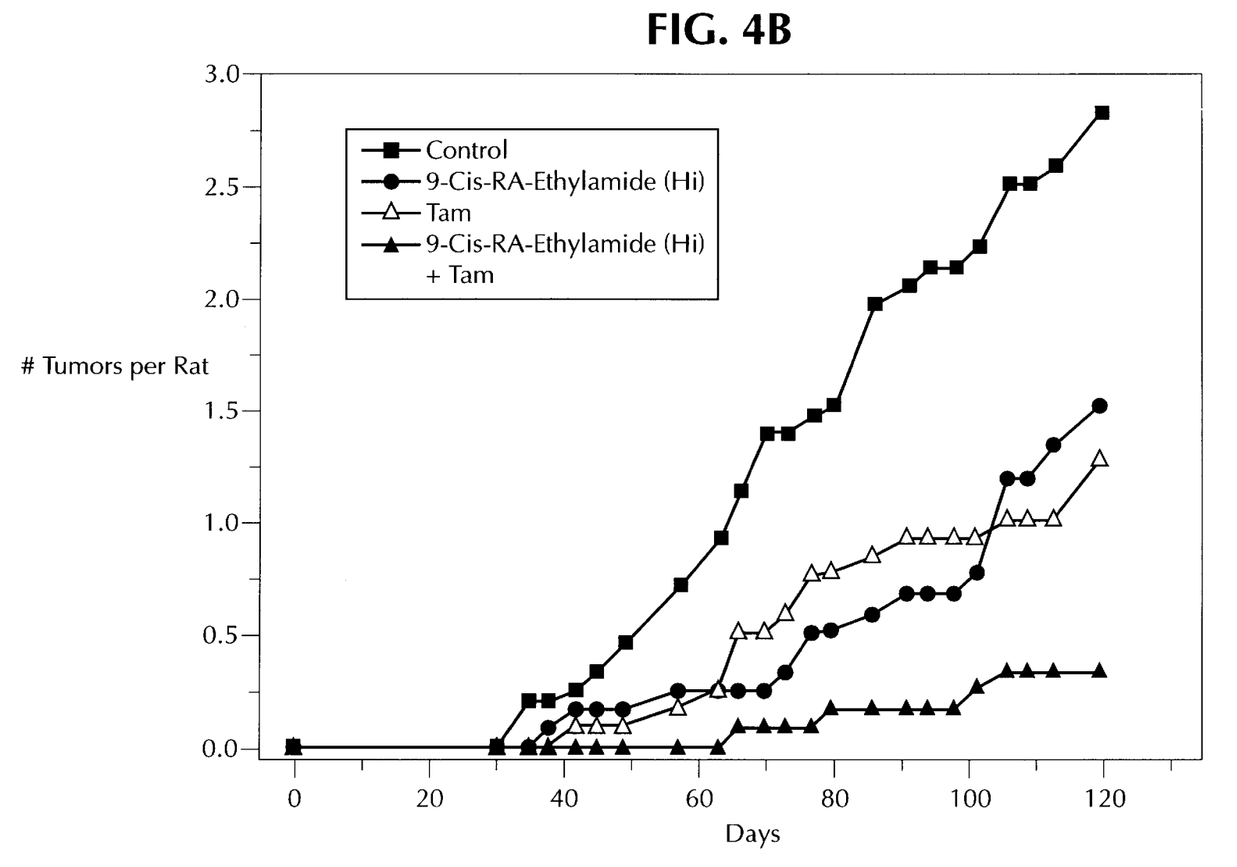
Figure 4C:
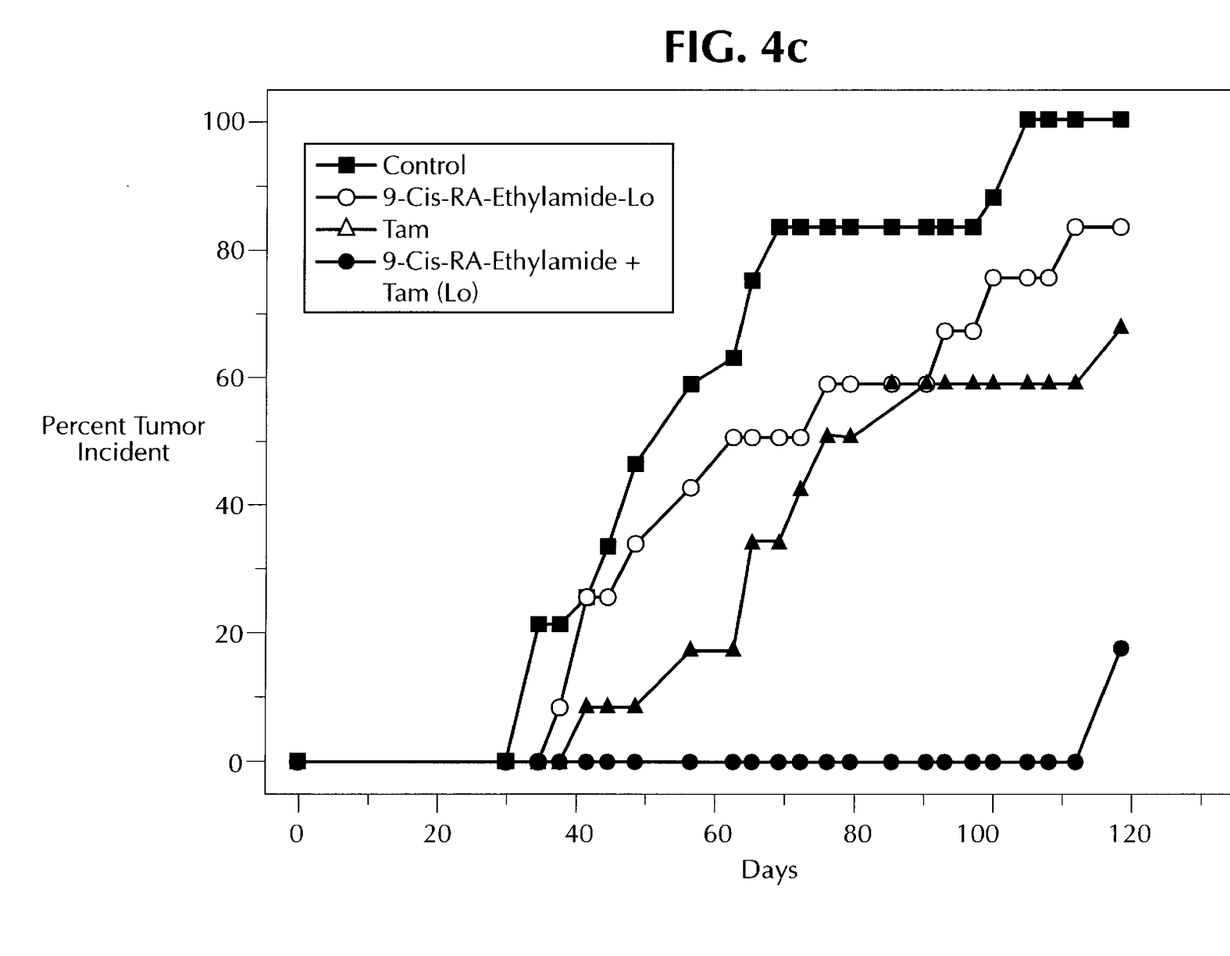
Figure 4D:
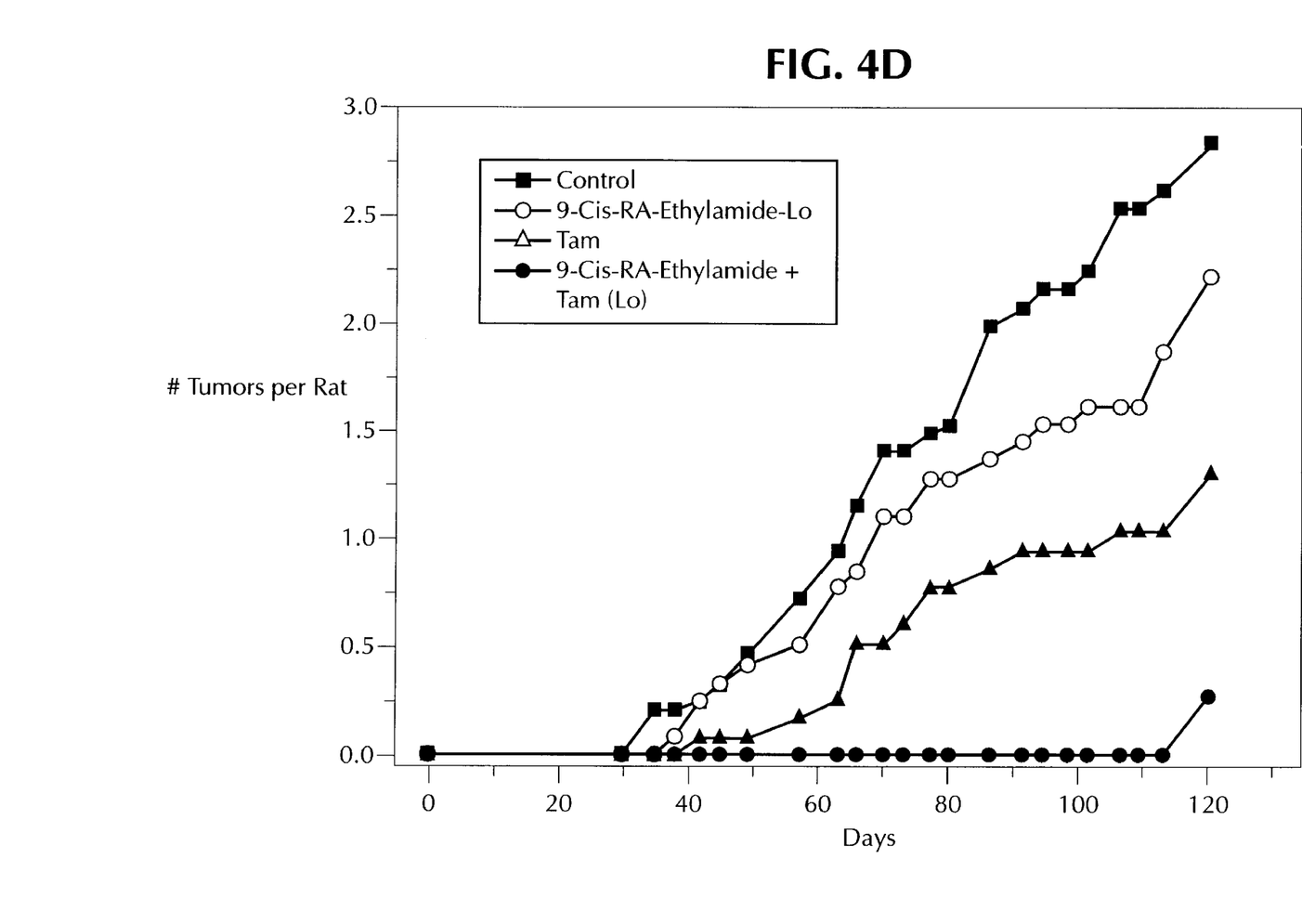

Several human breast cancer cell lines were analyzed to study their response to 9-cis-RA compared to atRA. As reported previously... *Chemistry, and Medicine,* 2nd edition, pp. 443–520, New York: Raven Press, 1994), we found that atRA inhibited $^3$H-thymidine incorporation in several differentiated (E-cad-positive) cell lines including MCF-7 (ATCC), T47D and ZR-75B, while it was essentially inactive in undifferentiated (E-cad-negative) lines such as MDA-231 (ATCC), MDA-453 (ATCC), MDA-436 (ATCC), and BUT-549 (ATCC). In the present study, the effects of 9-cis-RA was measured on the above cell lines and it was found that 9-cis-RA had activity essentially equivalent to that of atRA, again depending on the state of differentiation of the particular cell line. However, the growth of one relatively undifferentiated cell line, SKBR-3, which expressed very low levels of E-cadherin, was inhibited equivalently by both 9-cis-RA and atRA. Within 12 h of treatment with either 9-cis-RA or atRA ($10^{-7}$M), SKBR-3 cells exhibited a marked change in morphology (FIG. 2A–2B). This morphological change was accompanied by increased expression of E-cad at cell-cell contact sites.

It is shown herein, that 9-cis-retinoic acid (9-cis-RA) is a potent inhibitor of mammary carcinogenesis induced by N-nitroso-N-methylurea (NMU) in Sprague-Dawley rats. Rats were first treated with a single dose of NMU (50 mg/kg body weight) and then fed non-toxic levels of 9-cis-RA (120 or 60 mg/kg of diet). 9-cis-RA was highly effective in reducing tumor incidence, average number of tumors per rat, and average tumor burden, as well as extending tumor latency. For suppression of carcinogenesis in vivo, 9cisRA was much more potent than all-trans-retinoic acid (atRA), both as a single agent or in combination with TAM. Both retinoids had equivalent inhibitory effects on DNA synthesis in cultured human breast cancer cell lines. Both 9-cis-RA and atRA induce the expression of the adhesion molecule, E-cadherin, in the SK-BR-3 cell line. Loss of functional E-cad has been implicated in breast cancer progression (Oka, H., et al. Cancer Res., 53:1696–1701, 1993; Gamallo, C., et al. Am. J. Pathol., 142:987–993, 1993; Rasbridge, S. A., J. et al., Pathol., 169:245–250, 1993; Frixen, U. H., et al., J. Cell Biol., 113:173–185, 1991; Vleminckx, K., et al., Cell, 66:107–119, 1991; Sommers, C. L., et al., Cell Growth Differ., 2:365–372, 1991; D'souza, B., and Taylor-Papadimitriou, J. Proc. Natl. Acad. Sci. USA, in press, 1994).

In addition to showing its efficacy as a single agent, it has been shown herein that 9-cis-RA markedly enhances the chemopreventive activity of Tamoxifen (TAM), particularly when TAM is used at very low doses. The combination of 9-cis-RA with low levels of tamoxifen (TAM, fed at either 1.0 or 0.5 mg/kg of diet) was particularly effective; addition of 9-cis-RA to a TAM regimen doubled the number of animals that were tumor-free at autopsy and significantly diminished tumor number and tumor burden. The highest dose of TAM given to a rat in the present study is less than 20% of that given to a 60 kg woman receiving the standard 20 mg daily dose (for this calculation it was assumed that the rat weighs 250 grams and eats 10 grams of food daily). There is concern at present regarding the safety of chronic administration of the standard 20 mg daily dose of TAM, which is widely used in the adjuvant setting and is currently under study in long-term human chemoprevention trials. The present data suggest that it may be possible to lower the dose of TAM, and still retain efficacy if TAM were used in combination with a second agent, such as 9-cis-RA. Synergistic interaction of TAM and another retinoid, 4-hydroxyphenyl (4-HPR) retinamide, in another model of prevention of breast cancer has been shown previously (Ratko, T. A., et al. Cancer Res., 49:4472–4476, 1989), although the dose of 4-HPR was very high, and the benefit obtained was not as great as for 9-cis-RA. It has previously been reported that synthetic derivatives of vitamin D (deltanoids) can synergies with TAM in the NMU breast cancer model (Anzano, M. A., et al., Cancer Res., 54:1653–1656, 1994), however the suppressive effects of this combination were not as great as we have obtained here with 9-cis-RA plus TAM.

EXAMPLE 2

Prevention of Breast Cancer With 9 Retinoic Acid In Combination With Raloxifene

Materials And Methods

Mammary Carcinogenesis Studies

A standard protocol for induction of breast cancer in Sprague-Dawley rats was used as described in Example 1, with a single intravenous dose of NMU at 50 mg/kg body weight. Palpated tumors were confirmed at autopsy. 9-cis-retinoic acid (9-cis-RA) and Raloxifene (Eli Lily and Co., Indianapolis, IN) were incorporated in powdered lab chow as described in Example 1 and fed ad libitum beginning one week after injection with NMU. 9-cis-RA (KURARAY COMPANY, OSAKA, JAPAN) was provided at 0.2 mmoles/ kg of diet. Raloxifene was used at one of two doses: 20 mg/kg of diet (low) and 60 mg/kg of diet (high). The treatment protocol of rats with NMU and dosages used are summarized in Table 3.

TABLE 3

| NMU TREATMENT PROTOCOL AND DOSAGES | |
|---|---|
| Carcinogen Treatment | Sprague-Dawley rats 55–60 days old were injected with NMU (50 mg/Kg body weight) |
| Raloxifene | Hi dose = 60 mg/Kg of diet (3 mg/Kg BW (Body Weight)) Low dose = 20 mg/Kg of diet (1 mg/Kg BW) |
| 9-cis-RA | Dose = 0.2 millimole/Kg of diet |

Inhibition Of Mammary Carcinogenesis

Results were obtained in rats treated with NMU, using either 9-cis-RA alone or in combination with Raloxifene, to inhibit the development of mammary carcinogenesis. The experimental protocol and grouping of the animals is shown in Table 4. The results of the experiments are shown in FIGS. 3A-3D. As in Example 1, in all cases treatment with the chemopreventive agents began 1 week after a single i.v. injection of NMU. The data shows that 9-cis-RA in combination with Raloxifene; at high doses, effectively inhibits mammary carcinogenesis as assessed by the percent of tumor incidence in the animals (FIG. 3A) and the number of tumors per rat (FIG. 3B). 9-cis-RA in combination with Raloxifene at low dosages, as assessed by tumor incidence and number of tumors per rat (FIG. 3C and 3D respectively), also effectively inhibits mammary carcinogenesis. 9-cis-RA in combination with Raloxifene (low and high dosage) is more effective in preventing mammary carcinogenesis than either agent alone (FIGS. 3A–3D). Control animals (groups 1–6; Table 6) were normal.

TABLE 4

Experimental Protocol for Prevention of Breast Cancer In Rats by Raloxifene in Combination with 9-cis-RA

| GROUP | NMU | RALOXIFENE | RETINOIDS | # RATS |
|---|---|---|---|---|
| 1 | None | None | None | 3 |
| 2 | None | Raloxifene, Hi | — | 3 |
| 3 | None | Raloxifene, Lo | — | 3 |
| 4 | None | Raloxifene, Hi | 9-cis-RA | 3 |
| 5 | None | Raloxifene, Lo | 9-cis-RA | 3 |
| 6 | None | None | 9-cis-RA | 3 |
| 7 | 50 mg/Kg IV | None | None | 24 |
| 8 | 50 mg/Kg IV | Raloxifene, Hi | — | 12 |
| 9 | 50 mg/Kg IV | Raloxifene, Lo | — | 12 |
| 10 | 50 mg/Kg IV | Raloxifene, Hi | 9-cis-RA | 12 |
| 11 | 50 mg/Kg IV | Raloxifene, Lo | 9-cis-RA | 12 |
| 12 | 50 mg/Kg IV | None | 9-cis-RA | 12 |

EXAMPLE 3

Prevention of Breast Cancer In The Rat With A 9-cis-retinoic Acid Derivative As A Single Agent Or In Combination With Tamoxifen Materials and Methods Mammary Carcinogenesis Studies A standard protocol for induction of breast cancer in Sprague-Dawley Rats was used as described in Example 1, with a single intravenous dose of NMU at 50 mg/kg body weight. Palpated tumors were confirmed at autopsy. 9-cis-retinoic acid-ethylamide (9CE), and TAM were incorporated in powdered lab chow as described in Example 1 and fed ad libitum beginning one week after injection with NMU. 9CE was synthesized by conventional methodology (Stanford Research Institute, Menlo Park California) and was provided at either of two doses: 2 mmoles/kg of diet (Hi dose) or 1 mmole/kg of diet (lo dose). TAM (SIGMA CHEMICALS, ST. LOUIS, MO.) was used at a dose of 0.5 mg/kg of diet. The protocol for treatment of the animals with NMU and doses of 9CE and Tamoxifen is summarized in Table 5.

TABLE 5

Protocol For NMU Treatment of Rats and Dosages of 9CE And Tamoxifen

| | |
|---|---|
| Carcinogen Treatment | Sprague-Dawley rats 55–60 days old were injected with NMU (50 mg/Kg body Wt.) |
| 9-cis-retinoic Acid Ethylamide (9CE) | Hi dose = 2 mmoles/Kg of diet Lo dose = 1 mmole/Kg of diet |
| Tamoxifen | Dose = 0.5 mg/kg of diet |

The experimental protocol and grouping of the animals is shown in Table 6. The results of the experiments are shown in FIGS. 4A–4D. As in Example 1, in all cases treatment with the chemopreventive agents began 1 week after a single i.v. injection of NMU.

The data show that 9CE, at both hi and low doses, effectively inhibits mammary carcinogenesis (FIGS. 4A–4D) as assessed by the percent of tumor incidence and the number of tumors per rat. The combination of TAM and 9CE is superior to the use of either compound alone. Control animals (groups 1–6; Table 6) were normal.

TABLE 6

Protocol for Prevention of Breast Cancer in Rats by 9-Cis Retinoid Acid Ethylamide (9CE) Alone or in Combination with Tamoxifen
Protocol Breast #12

| Group | NMU | 9-Cis Retinoid Derivative | Tam | # of Rats |
|---|---|---|---|---|
| 1 | None | None | None | 3 |
| 2 | None | 9CE, Hi | — | 3 |
| 3 | None | 9CE, Lo | — | 3 |
| 4 | None | None, | 0.5 mg | 3 |
| 5 | None | 9CE, Hi | 0.5 mg | 3 |
| 6 | None | 9CE, Lo | 0.5 mg | 3 |
| 7 | 50 mg/kg, IV | None | None | 24 |
| 8 | 50 mg/kg, IV | 9CE, Hi | — | 12 |
| 9 | 50 mg/kg, IV | 9CE, Lo | — | 12 |
| 10 | 50 mg/kg, IV | None, | 0.5 mg | 12 |
| 11 | 50 mg/kg, IV | 9CE, Hi | 0.5 mg | 12 |
| 12 | 50 mg/kg, IV | 9CE, Lo | 0.5 mg | 12 |

EXAMPLE 4

Chemoprevention of Human Breast Cancer

In breast cancer patients, who are post-disease or post-surgery, 9-cis-retinoic acid may be administered as a chemopreventive or prophylactic measure. The 9-cis-retinoic acid may be administered in a pharmaceutical composition at a dosage of about 0.1 mg/kg to about 1000 mg/kg daily, preferably about 1 mg/kg to about 500 mg/kg daily or most preferred about 1 mg/kg/day to about 100 mg/kg/day.

Tamoxifen or Raloxifene may also be administered in conjunction with the 9-cis-retinoic acid or derivatives thereof. Dosages for Tamoxifen and Raloxifene may be based on the standard doses routinely used for these drugs.

Although the present invention has been described in some detail by uses of illustration and examples for purposes of clarity of understanding it will be obvious that certain modifications may be practical within the scope of the appended claims.

We claim:

1. A method of inhibiting cancer in an individual comprising administering to the individual an effective amount of 9-cis-retinoic acid or a derivative thereof and at least one of Tomoxifen or a derivative thereof, or Raloxifene or a derivative thereof.

2. The method of claim 1, wherein the 9-cis-retinoic acid derivative is an amide derivative.

3. The method of claim 2, wherein the 9-cis-retinoic acid derivative is 9-cis-retinoic acid ethylamide.

4. The method of claim 1, wherein the cancer is an opithelial cell cancer.

5. The method of claim 4, wherein the cancer is selected from the group consisting of breast cancer, prostate cancer, and colon cancer.

6. The method of claim 5, wherein the cancer is breast cancer.

7. The method of claim 1, wherein the effective amount of the 9-cis-retinoic acid is about 0.1 mg/kg/day to 1,000 mg/kg/day.

8. The method of claim 7, wherein the effective amount of the 9-cis-retinoic acid or derivative thereof is about 0.5 mg/kg/day to about 500 mg/kg/day.

9. The method of claim 1 wherein the effective amount of Raloxifene is about 0.05 mg/kg/day to about 50 mg/kg/day.

10. The method of claim 1 wherein the effective amount of Tamoxifen is about 20 mg daily to about 40 mg daily.

11. A composition of enhancing the activity of an estrogen modifying drug comprising 9-cis-retinoic acid or a derivative thereof and at least one of Tamoxifen or a derivative thereof, or Raloxifene or a derivative thereof.

12. The composition of claim 11 wherein the 9-cis-retinoic acid derivative is an amide derivative.

13. The composition of claim 11 wherein the 9-cis-retinoic acid derivative is 9-cis-retinoic acid ethylamide.

14. A pharmaceutical composition comprising Tamoxifen or a derivative thereof or, Raloxifene or a derivative thereof and a member selected from the group consisting of (i) 9-cis-retinoic acid, (ii) derivatives of 9-cis-retinoic; and (iii) a combination of (i) and (ii), and a pharmaceutically acceptable carrier.

15. A method of inhibiting cancer in an individual comprising administering to the individual a therapeutically effective amount of the composition of claim 14.

16. A pharmaceutical composition for inhibiting cancer comprising 9-cis-retinoic acid or a derivative thereof and at least one of Tamoxifen or Raloxifene or a derivative thereof and a pharmaceutically acceptable carrier.

17. The pharmaceutical composition of claim 16, wherein said 9cis retinoic acid derivative is an amide derivative.

18. The pharmaceutical composition of claim 17, wherein said 9-cis-retinoic acid derivative is 9-cis-retinoic acid ethylamide.

19. A method of inhibiting cancer in an individual comprising administering to the individual a therapeutically effective amount of the composition of claim 16.

20. The composition of claim 14 wherein the 9-cis-retinoic acid derivative is an amide derivative.

21. The composition of claim 20 wherein the 9-cis-retinoic acid amide derivative is 9-cis-retinoic acid ethylamide.

22. The composition of claim 14 comprising Tamoxifen or Raloxifene.

* * * * *